US009907843B2

(12) United States Patent
Bremont et al.

(10) Patent No.: US 9,907,843 B2
(45) Date of Patent: Mar. 6, 2018

(54) RECOMBINANT NOVIRHABDOVIRUS USABLE AS AN ANTIGEN VECTOR

(71) Applicant: Institut National de la Recherche Agronomique, Paris (FR)

(72) Inventors: Michel Bremont, Sevres (FR); Angella Nzonza, Ponthierry (FR)

(73) Assignee: Institut National de la Recherche Agronomique, Paris (FR)

(*) Notice: Subject to any disclaimer, the term of this patent is extended or adjusted under 35 U.S.C. 154(b) by 0 days.

(21) Appl. No.: 14/435,981

(22) PCT Filed: Oct. 8, 2013

(86) PCT No.: PCT/IB2013/059207
§ 371 (c)(1),
(2) Date: Apr. 15, 2015

(87) PCT Pub. No.: WO2014/060905
PCT Pub. Date: Apr. 24, 2014

(65) Prior Publication Data
US 2015/0265699 A1   Sep. 24, 2015

(30) Foreign Application Priority Data
Oct. 15, 2012 (FR) ..................... 12 59815

(51) Int. Cl.
*A61K 39/205* (2006.01)
*A61K 39/12* (2006.01)
(Continued)

(52) U.S. Cl.
CPC ............ *A61K 39/205* (2013.01); *A61K 39/12* (2013.01); *C12N 7/00* (2013.01); *C12N 15/86* (2013.01); *A61K 2039/5256* (2013.01); *A61K 2039/70* (2013.01); *C07K 2319/02* (2013.01); *C07K 2319/03* (2013.01); *C07K 2319/40* (2013.01); *C12N 2760/20021* (2013.01); *C12N 2760/20034* (2013.01); *C12N 2760/20043* (2013.01)

(58) Field of Classification Search
None
See application file for complete search history.

(56) References Cited

U.S. PATENT DOCUMENTS 6,497,873 B1 * 12/2002 Whitt ................. C07K 14/005
424/93.2
2006/0063250 A1   3/2006 Bremont et al.

FOREIGN PATENT DOCUMENTS

WO      03/097090 A1   11/2003
WO   2004/026338 A1    4/2004
(Continued)

OTHER PUBLICATIONS

International Search Report issued in corresponding International Patent Application No. PCT/IB2013/059207 dated Jan. 28, 2014.
(Continued)

*Primary Examiner* — Janet L Andres
*Assistant Examiner* — Stuart W Snyder
(74) *Attorney, Agent, or Firm* — Morgan, Lewis & Bockius LLP

(57) ABSTRACT

The invention relates to a recombinant novirhabdovirus expressing a chimeric protein comprising the sequence of an antigen of interest flanked, at the N-terminus, by a signal peptide, and at the C-terminus, by a polypeptide comprising at least one portion of the transmembrane domain of a rhabdovirus G protein. Said recombinant novirhabdovirus can be used especially for inducing an immune response to the antigen of interest.

11 Claims, 1 Drawing Sheet

US 9,907,843 B2
Page 2

(51) Int. Cl.
   *C12N 15/86*   (2006.01)
   *C12N 7/00*    (2006.01)
   *A61K 39/00*   (2006.01)

(56) References Cited

FOREIGN PATENT DOCUMENTS

| WO | WO 2007/144773 | A2 | * | 6/2007 | ............ | C12N 15/09 |
| WO | 2007/144773 | A2 | | 12/2007 | | |
| WO | WO 2007/144773 | A2 | * | 12/2007 | ............ | C12N 15/09 |
| WO | WO 2009/019612 | A2 | * | 12/2009 | ............ | A61K 39/21 |

OTHER PUBLICATIONS

Schnell et al., "Foreign glycoproteins expressed from recombinant vesicular stomatitis viruses are incorporated efficiently into virus particles," Proceedings of the National Academy of Sciences, 93: 11359-11365 (1996).
Schlehuber et al., "Prediction and Identification of a Permissive Epitope Insertion Site in the Vesicular Stomatitis Virus Glycoprotein," Journal of Virology, 78: 5079-5087 (2004).
Desmezieres et al., "Lyssavirus glycoproteins expressing immunologically potent foreign B cell and cytotoxic T lymphocyte epitopes as prototypes for multivalent vaccines," Journal of General Virology: 80: 2343-2351 (1999).

* cited by examiner

Figure 1

Figure 2

A — Anti-DIII WNV

B — Anti-G vHSV (Novirhabdovirus)

RECOMBINANT NOVIRHABDOVIRUS USABLE AS AN ANTIGEN VECTOR

SEQUENCE LISTING SUBMISSION VIA EFS-WEB

A computer readable text file, entitled "045636-5279-SequenceListing.txt" created on or about Apr. 14, 2015, with a file size of about 2 kb contains the sequence listing for this application and is hereby incorporated by reference in its entirety.

The present invention relates to recombinant novirhabdoviruses usable as antigen vectors, and in particular vectors for non-glycosylated antigenic proteins, for inducing an immune response against said antigens.

Novirhabdoviruses are negative RNA viruses of the rhabdovirus family.

Rhabdoviruses are enveloped viruses. The virion comprises a nucleocapsid with helical symmetry, resulting from the assembly of N protein molecules around the genomic RNA strand, and in which are associated L and P protein molecules. The envelope which covers the nucleocapsid consists of a double lipid layer of cell origin, the internal face of which is coated with the M protein, and in which are inserted spikes formed from glycoprotein G trimers, involved in the attachment of the virus to the infected cell, and its fusion with the cell membrane. The rhabdovirus G glycoprotein is, in its mature form, a polypeptide of approximately 500 amino acids, consisting of an ectodomain of approximately 435 to approximately 450 amino acids in the N-terminal position, followed by a transmembrane domain of 21 to 23 amino acids, and an intravirion domain (also called intracytoplasmic domain) of approximately 25 to approximately 45 amino acids. It is synthesized in the cytoplasm of infected cells in the form of a precursor of 505 to 525 amino acids, the signal peptide of which is then cleaved in the endoplasmic reticulum.

The Novirhabdovirus genus comprises various species that are pathogenic to aquatic animals, in particular fish.

The standard species of the genus is the infectious hematopoietic necrosis virus (IHNV) which is the etiological agent of a serious disease in several species of salmonids. Other species of the genus are the hirame rhabdovirus (HIRRV), the viral hemorrhagic septicemia virus (VHSV) and the snakehead rhabdovirus (SHRV).

The structure of the novirhabdovirus genome is close to that of mammalian rhabdoviruses, but differs therefrom by virtue of the presence of an additional gene, encoding a nonstructural protein, called NV (for "nonvirion") protein.

The novirhabdovirus genome thus comprises six genes, the organization of which can be represented diagrammatically as follows:

3'-N-P-M-G-NV-L-5'

N represents a gene encoding the nucleoprotein associated with the viral RNA, P represents the gene encoding the phosphoprotein associated with the viral polymerase, M represents the gene encoding the matrix protein, G represents the gene encoding the envelope glycoprotein G (also called spike protein), NV represents the gene encoding the NV protein, and L represents the gene encoding the RNA-dependent viral RNA polymerase.

These genes are separated by intergenic regions: each of them comprises a transcription initiation signal for the gene located downstream of said signal, and a transcription termination and polyadenylation signal, which allows transcription of the genes into individual mRNAs.

It has been shown that novirhabdoviruses can be used as expression vectors for heterologous genes, and in particular for vaccine antigens.

Reverse genetic systems, similar to those which exist for mammalian rhabdoviruses, are in fact available for producing recombinant novirhabdoviruses. Conventionally, these systems are based on the cotransfection of a host cell expressing an RNA polymerase (generally the T7 RNA polymerase) with the complementary DNA (cDNA) of the complete viral genome, and expression vectors encoding the N, P and L proteins of the viral replication complex.

Various approaches have been used to introduce foreign genes in these recombinant novirhabdoviruses, for the purpose of using said novirhabdoviruses as viral vectors.

A first approach is based on the replacement of an endogenous novirhabdoviruses gene with a heterologous gene. For example, it has thus been shown, in IHNV, VHSV and SHRV, that the glycoprotein G gene can be replaced with that of another novirhabdovirus, and that the NV gene can be deleted and replaced with a foreign gene (Biacchesi et al., J Virol, 74, 11247-53, 2000; Biacchesi et al., J Virol, 76, 2881-9, 2002; Biacchesi et al., J Virol, 84, 10038-50, 2010; Alonso et al., Journal of Virology, 78, 5875-82, 2004; PCT application WO 2003/097090).

A second approach consists in inserting one or more genes into one or more of the intergenic regions of the viral genome, in the form of one or more additional transcription unit(s), each transcription unit comprising a transcription initiation signal, followed by the coding sequence of the protein of interest to be expressed, this coding sequence itself being followed by a transcription termination/polyadenylation signal.

This approach has been used in particular in IHNV and VHSV, to express, in vivo, various reporter genes (Harmache et al., J Virol, 80, 3655-9, 2006; Biacchesi et al., J Virol, 84, 10038-50, 2010). It has also made it possible to express vaccine antigens; PCT application WO 2007/144773 describes the construction of recombinant IHNVs comprising from 1 to 3 intergenic inserts expressing antigens of various viruses pathogenic to salmonids, and shows that these recombinant IHNVs are capable of multiplying normally in cell cultures, and can induce a protective immune response against the viruses concerned, when they are used to immunize young trout. In addition, when one of these recombinant IHNVs expressing a heterologous antigen is injected in vivo in mice, it is incapable of replicating therein, but induces, however, an antibody response directed in particular against the heterologous antigen.

Novirhabdoviruses thus have many advantages as heterologous antigen expression vectors.

In order to further improve the effectiveness of the antigenic response directed against heterologous antigens expressed by novirhabdoviruses, it is desirable for these antigens to be exposed at the surface of the viral particles. However, the inventors have noted that, in the case of the recombinant novirhabdoviruses previously described, only certain antigens, of glycoprotein nature and capable of naturally inserting into cell membranes, are present at the surface of the viral particles.

In seeking to remedy this drawback, the inventors have noted that, when a gene encoding a chimeric polypeptide containing the sequence of an antigen of interest, flanked at its N-terminal end by the sequence of the signal peptide of a novirhabdovirus G protein, and at its C-terminal end by the sequence of the transmembrane domain of a novirhabdovirus G protein, is inserted into the genome of a novirhabdovirus, the expression of this chimeric gene results in the incorporation of the mature form of its translation product into the viral envelope, without this incorporation interfering with the assembly of the virion, or with its capacity to infect cells in culture and to replicate therein.

A subject of the present invention is a recombinant novirhabdovirus containing in its genome, in addition to the genes encoding the endogenous N, P, M, G and L proteins of said novirhabdovirus, an exogenous gene encoding a chimeric protein, said chimeric protein being characterized in that it comprises the sequence of an antigenic protein of interest fused, at its N-terminal end, with a signal peptide and, at its C-terminal end, with a rhabdovirus G protein sequence fragment, said fragment comprising the transmembrane domain of said rhabdovirus G protein or a portion thereof. In the case of a portion of the transmembrane domain, this portion generally comprises at least 15, preferably at least 16, and in increasing order of preference at least 17, 18, 19 or 20 consecutive amino acids of said domain. It will preferably be a C-terminal portion of said transmembrane domain.

The transmembrane domain of the G protein of a rhabdovirus is defined herein as the region of the G protein located between the ectodomain and the intravirion domain of said protein. The transmembrane domain can be easily located by those skilled in the art in the sequence of a G protein, for example on the basis of the annotations that appear in databases, or, where appropriate, using software for predicting protein domains, such as TMHMM (http://www.cbs.dtu.dk/services/TMHMM) or InterProScan (http://www.ebi.ac.uk/Tools/pfa/iprscan/).

By way of nonlimiting examples, according to the indications provided by the Uniprot/Swissprot database, the transmembrane domain of the G protein corresponds, in novirhabdoviruses, to amino acids 462-482 of the sequence of the G protein precursor in the case of VHSV, of IHNV and of the hirame rhabdovirus, and to amino acids 464-486 in the case of SHRV. In rhabdoviruses other than novirhabdoviruses, this transmembrane domain corresponds to amino acids 460-480 of the sequence of the G protein precursor in the case of the rabies virus (Lyssavirus), to amino acids 468-488 in the case of the vesicular stomatitis virus (Vesiculovirus), and to amino acids 462-482 in the case of the spring viremia of carp virus (Vesiculovirus).

Advantageously, said transmembrane domain is chosen from those of the G proteins of lyssavirus, of vesiculovirus and of novirhabdovirus. Entirely preferably, it is the transmembrane domain of the G protein of a novirhabdovirus.

Said G protein fragment may also comprise, following the transmembrane domain or the portion thereof, the intravirion domain of a rhabdovirus G protein, or a portion of said intravirion domain. Generally, for reasons of convenience for constructing the chimeric gene, said intravirion domain will be derived from the G protein in the same rhabdovirus as the transmembrane domain; it is, however, possible to combine a transmembrane domain and an intravirion domain (or the portions thereof) derived from different rhabdoviruses. In the case of a portion of the intravirion domain, it preferably comprises at least 3, advantageously at least 4, and in increasing order of preference at least 5, 6, 7, 8, 9 or 10 consecutive amino acids of said domain. It will preferably be an N-terminal portion of said domain.

Although it is preferred for the C-terminal end of the antigenic protein of interest to be directly fused to the N-terminal end of the transmembrane domain, it is, however, possible to envision, in certain cases, that some C-terminal amino acids of the ectodomain (generally less than 20, preferably less than 10, and advantageously less than 5) are present between the antigenic protein of interest and the transmembrane domain.

The signal peptide may be any peptide which allows the trafficking of the chimeric protein into the endoplasmic reticulum of the cell infected with the novirhabdovirus, followed by the cleavage of said signal peptide. A large number of signal peptides that are usable for this purpose are known in themselves to those skilled in the art. Use may, as appropriate, be made of the endogenous signal peptide of the antigenic protein of interest that it is desired to express, if it possesses one. Advantageously, use may be made of the signal peptide of the G protein of a rhabdovirus, and in particular of a novirhabdovirus; it is not essential for this signal peptide to be derived from the G protein of the same virus as the transmembrane domain and/or as the intravirion domain.

The antigenic protein of interest may be any protein or any protein fragment with respect to which it is desired to induce a humoral and/or cellular immune response. Particularly advantageously, said protein or said fragment is non-glycoprotein in nature, i.e. it is a question of polypeptides which are not glycosylated when they are expressed in animal cells.

It may in particular be an antigen derived from a viral, bacterial or fungal pathogen, a protozoan parasite, or a tumor antigen, or else a recombinant protein combining various antigenic fragments, derived from the same antigen or from different antigens.

The size of this antigenic protein may vary by a few amino acids to a few hundred amino acids; preferably, it will be from 100 to 600 amino acids, and entirely preferably from 300 to 600 amino acids.

Particularly advantageously, said antigenic protein is non-glycoprotein in nature, i.e. it is a polypeptide which is not glycosylated when it is expressed in an animal cell.

By way of nonlimiting example of an antigenic protein of non-glycoprotein nature, mention will be made of flavivirus E protein domain III. Although the whole E protein is a glycoprotein, domain III thereof contains no glycosylation site.

A recombinant novirhabdovirus in accordance with the invention can be obtained from any novirhabdovirus, in particular IHNV, VHSV, HIRRV or SHRV. Preferred novirhabdoviruses are IHNV and VHSV.

According to a first embodiment of a recombinant novirhabdovirus in accordance with the invention, the gene encoding the chimeric protein is inserted as a replacement for the endogenous NV gene of said novirhabdovirus. Recombinant novirhabdoviruses in accordance with this first embodiment can be constructed as described, for example, by Biacchesi et al. (2000, 2002, 2010, mentioned above) or Alonso et al. (2004, mentioned above) or in PCT application WO 2003/097090.

According to a second embodiment of a recombinant novirhabdovirus in accordance with the invention, it retains the endogenous NV gene, and the gene encoding the chimeric protein is inserted into an additional transcription unit placed in an intergenic region of the viral genome. Recombinant novirhabdoviruses in accordance with this second embodiment can be constructed as described, for example, by Biacchesi et al. (2010, mentioned above) or Harmache et al. (2006, mentioned above) or in PCT application WO 2007/144773.

In accordance with this second embodiment, said novirhabdovirus may contain several additional transcription units, each of which contains an exogenous gene encoding a chimeric protein. Preferably, said novirhabdovirus contains two additional transcription units, and entirely preferably three additional transcription units. Advantageously, said chimeric proteins differ from one another at least by virtue of the nature of the antigen of interest, and optionally by virtue of that of the signal peptide and/or the transmembrane domain and/or the intravirion domain.

A subject of the present invention is also recombinant DNA constructs which make it possible to obtain a novirhabdovirus in accordance with the invention.

In this context, the present invention encompasses in particular the cDNA of the genome of a recombinant novirhabdovirus in accordance with the invention, and also any recombinant vector comprising said cDNA.

A subject of the present invention is also the uses of a recombinant novirhabdovirus in accordance with the invention, for inducing a humoral and/or cellular immune response against the antigenic protein of interest expressed by said novirhabdovirus.

In particular, a subject of the present invention is a recombinant novirhabdovirus in accordance with the invention, for use as a medicament, and in particular as a vaccine.

The vaccines containing a recombinant novirhabdovirus in accordance with the invention can be used in fish, and in particular salmonids, such as farmed trout and salmon, according to the methods described in PCT application WO 2003/097090 or in PCT application WO 2007/144773.

The recombinant novirhabdoviruses in accordance with the invention, and in particular those which replicate only at low temperature, such as IHNV and VHSV, are usable for obtaining vaccines, not only in fish, but also in other animals, including birds and mammals, and in particular members of the ovine race, cattle, pigs, members of the horse family, members of the canine family, members of the cat family, and primates, in particular humans. Indeed, although novirhabdoviruses are incapable of replicating in a homoeothermic animal, they are capable of inducing a strong immune response against a heterologous antigen of interest presented at the surface of the viral particle.

In this context, the novirhabdoviruses in accordance with the invention can be used as antiviral, antibacterial, antifungal or antitumor vaccines, depending on the nature of the antigen of interest chosen.

These vaccines can be formulated for use parenterally, for example intradermally, intramuscularly or subcutaneously, orally, or mucosally, for example intranasally. The amount of recombinant viruses for a vaccine dose is chosen so as to enable a level of expression of the antigenic protein of interest that is sufficient to induce an immune response against this protein. It can be determined by those skilled in the art in particular according to the nature of said antigenic protein, to the species and the age of the subject to be vaccinated, and to the type of immune response (cellular or humoral) that it is desired to favor.

A subject of the present invention is also the use of a recombinant novirhabdovirus in accordance with the invention, for preparing antibodies directed against the antigenic protein of interest expressed by said novirhabdovirus. These antibodies can be obtained by the conventional methods comprising the immunization of a non-human animal with a recombinant novirhabdovirus in accordance with the invention, and the recovery of the serum thereof (for the production of polyclonal antibodies) or of the lymphocytic cells thereof (for the production of monoclonal antibodies).

The present invention will be understood more clearly from the additional description which follows, which refers to nonlimiting examples of construction of a recombinant novirhabdovirus in accordance with the invention.

EXAMPLE 1

Construction of a Recombinant Novirhabdovirus Containing a Gene Encoding a Chimeric Protein Comprising Domain III Of West Nile Virus (wnv) Glycoprotein E The constructions were carried out using the pVHSV plasmid, described by Biacchesi et al. (2010, mentioned above). This plasmid contains the complete cDNA of the genome of a VHSV (strain 23-75, GenBank FN665788), cloned downstream of the T7 phage RNA polymerase promoter and upstream of a ribozyme sequence of the hepatitis δ virus and of the T7 phage RNA polymerase transcription terminator, in the pBlueScript SK vector (Stratagene).

The pVHSV plasmid contains a unique PsiI restriction site in the intergenic region between the N and P genes. This site is used to insert an additional transcription unit, containing a sequence encoding a fusion protein made up of the sequence of domain III of the West Nile Virus glycoprotein E (GenBank AF481864) preceded by the signal peptide of the VHSV G protein (strain 23-75, GenBank CBJ23832.1.), and followed by the 42 C-terminal amino acids of the VHSV G protein (strain 23-75).

The construction of this additional transcription unit is described in detail hereinafter.

The sequence encoding domain III of the West Nile Virus glycoprotein E, that encoding the signal peptide of the VHSV G protein, and that encoding the 42 C-terminal amino acids of the VHSV G protein were amplified by PCR using appropriate primers.

A first PCR amplification was carried out on the West Nile Virus cDNA, using the following primers:

SPSHVDIIIF:
(SEQ ID NO: 1)
5'-<u>ACTAGT</u>ATGGACACCACGATCACCACTCCGCTCATTCTCATTCTGAT

CACCTGCGGAGCA<u>GCTAGC</u>GGAACAACCTATGGCGTCTGTTCAAAGG-

3', which contains an SpeI site (ACTAGT) and an

NheI site (GCTAGC)
and

DIIISHVTMR:
(SEQ ID NO: 2)
5'-GGCCCCTCCCACAACCCCCATCCCAGATAACGCTCCTTTGAGGGTGG

TTGTAAAGG-3'.

A second PCR amplification was carried out on the VHSV cDNA, using the following primers:

DIIITMSHVF:
(SEQ ID NO: 3)
5'-CCTTTACAACCACCCTCAAAGGAGCGTTATCTGGGATGGGGGTTGTG

GGAGGGGCC-3',
and

SHVTMR:
(SEQ ID NO: 4)
5'-<u>TACGTA</u>TCAGACCGTCTGACTTCTAGAGAACTGC-3', which contains an SnaBI site (TACGTA).

The two amplification products were mixed, and a third PCR amplification was carried out on the mix, using the primers:

SPSHVF:
(SEQ ID NO: 5)
5'-ACTAGTATGGACACCACGATCACCACTCCGC-3', which contains an SpeI site (ACTAGT),
and (SEQ ID NO: 4)
SHVTMR.

The product of this third amplification (SPg-DIII-TMg), which contains the sequence encoding the signal peptide of the VHSV G protein, in reading frame with that encoding domain III of the West Nile Virus glycoprotein E, and that encoding the 42 C-terminal amino acids of the VHSV G protein, was cloned into a pJet1.2 vector (Fermentas). The SPg-DIII-TMg insert was excised from this vector by SpeI/SnaBI digestion and cloned, in place of the tdTomato gene, into the pVSHV-dTomato plasmid (described by Biacchesi et al., 2010, mentioned above) previously digested with SpeI/SnaBI, so as to obtain the final construct pSHV-SPg-DIII-TMg.

Recombinant Novirhabdovirus Production:

Three expression plasmids comprising respectively the genes encoding the nucleoprotein N, the phosphoprotein P, and the RNA-dependent RNA polymerase L of VHSV were constructed, as described by Biacchesi et al. (2010, publication mentioned above). These constructs are respectively called pT7-N, pT7-P and pT7-L.

The pVHSV plasmid or the pVHSV-SPg-DIII-TMg plasmid, at a dose of 1 μg, and the 3 pT7-N, pT7-P and pT7-L plasmids, at respective doses of 0.25 μg. 0.2 μg and 0.2 μg, are introduced, by transfection in the presence of lipofectamine (Gibco-BRL), into EPC cells previously infected with a recombinant vaccinia virus expressing the T7 phage RNA polymerase (vTF7-3, Fuerst et al., Proc. Natl. Acad. Sci. USA, 92, 4477-4481, 1986).

After transfection, the cells are incubated for 5 hours at 37° C. and then washed with MEM culture medium (serum free) and incubated for 7 days at 14° C. in MEM culture medium containing 2% of foetal calf serum. The cells and the supernatant are frozen/thawed, and clarified by centrifugation for 10 minutes at 10 000 revolutions/min. The supernatant is used at the 1/10 dilution to infect a layer of EPC cells (Epithelioma Papulosum Cyprini cells, derived from carp epithelial cells). The viruses are produced in the supernatant 3-4 days post-infection.

The viruses obtained are respectively called rVHSV, in the case of the virus possessing the genome of the wild-type virus, and rVHSV-SPg-DIII-TMg in the case of the virus containing the gene encoding the fusion protein.

Viral stocks of each of the viruses produced were formed by successive passages in cell culture of the supernatant taken 7 days after transfection (PO supernatant) on EPC cells. The cells are infected at a multiplicity of infection (MOI) of 1. After 3 passages, the supernatants were removed at various times post-infection, and titrated by limiting dilution in order to establish a growth curve.

The growth curves established for the rVHSV and rVHSV-SPg-DIII-TMg viruses show that the rVHSV-SPg-DIII-TMg virus multiplies in cell culture as well as the rVHSV virus.

The expression of domain III of the West Nile Virus glycoprotein E in the cells infected with rVHSV-SPg-DIII-TMg was verified at 2 days post-infection, by means of an indirect immunofluorescence test using an anti-DIII monoclonal antibody, on live infected cells or infected cells fixed with alcohol/acetone.

EXAMPLE 2

Exression of Domain III of the West Nile Virus Glycoprotein E at the Surface of the Novirhabdovirus EPC cells were infected as described in example 1 above, with the rVHSV virus or with the rVHSV-SPg-DIII-TMg virus.

Three days after the infection, the culture supernatant was recovered, and the viruses were purified on a sucrose gradient using this supernatant.

The viral proteins were separated by SDS-PAGE electrophoresis and visualized after staining with Coomassie blue or after Western blot transfer and incubation with a monoclonal antibody directed against domain III of the WNV glycoprotein E.

The results are shown in FIG. 1.
Legend of FIG. 1:
A: Left-hand panel: SDS PAGE gel, stained with Coomassie blue, of the rVHSV and rVHSV-SPg-DIII-TMg viruses purified on a sucrose gradient before transfer for Western blot;
right-hand panel: Western blot transfer with the monoclonal antibody directed against domain III of the WNV glycoprotein E;
B: SDS PAGE Gels of purified virus stained with Coomassie blue.
M: Molecular weight marker,
1: rVHSV
2: rVHSV-SPg-DIII-TMg.

These results show that domain III of the WNV glycoprotein E is strongly expressed in the particles of the rVHSV-SPg-DIII-TMg virus.

The purified rVHSV-SPg-DIII-TMg viral particles were also observed by electron microscopy after immunolabeling with colloidal gold using either an antibody directed against domain III of the WNV glycoprotein E, or an antibody directed against the VHSV glycoprotein G.

The results are shown in FIG. 2. The black dots at the surface of the viral particles indicate the presence of domain III of the WNV glycoprotein E (FIG. 2A), and also of the VHSV glycoprotein G (FIG. 2B) at the surface of the rVHSV-SPg-DIII-TMg viruses.

This shows that the antigen of interest is very strongly and very effectively expressed at the surface of the viral particles.

The invention claimed is:

1. A recombinant novirhabdovirus, the genome of which comprises the genes encoding the endogenous N, P, M, G and L proteins of said novirhabdovirus, and an exogenous gene encoding a chimeric protein, wherein said chimeric protein comprises the sequence of an antigenic protein of interest fused, at its N-terminal end, with a novirhabdovirus G protein signal peptide and, at its C-terminal end, with a novirhabdovirus G protein sequence fragment, said fragment comprising the transmembrane domain of said novirhabdovirus G protein or a portion thereof, said portion of the transmembrane domain comprises at least 15 consecutive C-terminal amino acids of said domain and wherein said antigenic protein of interest is not a glycoprotein.

2. The recombinant novirhabdovirus as claimed in claim 1, further comprising, the intravirion domain of a novirhabdovirus G protein, or a portion of said intravirion domain, said intravirion domain or said portion thereof being C-terminal to the transmembrane domain or the portion thereof, and said intravirion domain or the portion thereof following said transmembrane domain or the portion thereof.

3. The recombinant novirhabdovirus as claimed in claim 2, wherein said portion of the intravirion domain comprises at least three consecutive N-terminal amino acids of said domain.

4. The recombinant novirhabdovirus as claimed in claim 1, wherein said recombinant novirhabdovirus is devoid of the endogenous NV gene, and in that the gene encoding the chimeric protein is inserted as a replacement for said NV gene.

5. The recombinant novirhabdovirus as claimed in claim 1, wherein said recombinant novirhabdovirus contains the endogenous NV gene, and in that the gene encoding the chimeric protein is inserted into an additional transcription unit placed in an intergenic region of the viral genome.

6. The recombinant novirhabdovirus as claimed in claim 5, further comprising at least two additional transcription units, each of which comprising an exogenous gene encoding-said chimeric protein.

7. The recombinant novirhabdovirus as claimed in claim 1, wherein the recombinant novirhabdovirus is chosen from an infectious hematopoietic necrosis virus and a viral hemorrhagic septicaemia virus.

8. An isolated cDNA encoding the genome of a recombinant novirhabdovirus as claimed in claim 1.

9. A method of inducing an immune response in a subject, comprising administering to the subject a vaccine comprising the recombinant novirhabdovirus of claim 1, wherein the immune response is directed against the antigen of interest expressed by said novirhabdovirus.

10. The method of claim 9 wherein said vaccine is selected the group consisting of an antiviral vaccine, an antibacterial vaccine, an antifungal vaccine, an antiparasitic vaccine and an antitumor vaccine.

11. A method of producing antibodies in a subject, comprising administering to the subject the recombinant novirhabdovirus of claim 1, wherein the antibodies are directed against the antigen of interest expressed by said novirhabdovirus.

* * * * *

SEQUENCE LISTING

<160> NUMBER OF SEQ ID NOS: 5

<210> SEQ ID NO 1
<211> LENGTH: 94
<212> TYPE: DNA
<213> ORGANISM: Artificial Sequence

```
<220> FEATURE:
<223> OTHER INFORMATION: PCR primer

<400> SEQUENCE: 1
actagtatgg acaccacgat caccactccg ctcattctca ttctgatcac ctgcggagca    60
gctagcggaa caacctatgg cgtctgttca aagg                               94

<210> SEQ ID NO 2
<211> LENGTH: 56
<212> TYPE: DNA
<213> ORGANISM: Artificial Sequence
<220> FEATURE:
<223> OTHER INFORMATION: PCR primer

<400> SEQUENCE: 2
ggcccctccc acaaccccca tcccagataa cgctcctttg agggtggttg taaagg       56

<210> SEQ ID NO 3
<211> LENGTH: 56
<212> TYPE: DNA
<213> ORGANISM: Artificial Sequence
<220> FEATURE:
<223> OTHER INFORMATION: PCR primer

<400> SEQUENCE: 3
cctttacaac caccctcaaa ggagcgttat ctgggatggg ggttgtggga ggggcc       56

<210> SEQ ID NO 4
<211> LENGTH: 34
<212> TYPE: DNA
<213> ORGANISM: Artificial Sequence
<220> FEATURE:
<223> OTHER INFORMATION: PCR primer

<400> SEQUENCE: 4
tacgtatcag accgtctgac ttctagagaa ctgc                               34

<210> SEQ ID NO 5
<211> LENGTH: 31
<212> TYPE: DNA
<213> ORGANISM: Artificial Sequence
<220> FEATURE:
<223> OTHER INFORMATION: PCR primer

<400> SEQUENCE: 5
actagtatgg acaccacgat caccactccg c                                  31
```